United States Patent
Kumar et al.

[11] Patent Number: 5,196,635
[45] Date of Patent: Mar. 23, 1993

[54] OLIGOMERIZATION OF ALPHA-OLEFIN

[75] Inventors: Govind Kumar; Mark A. Davis, both of Baton Rouge, La.

[73] Assignee: Ethyl Corporation, Richmond, Va.

[21] Appl. No.: 912,050

[22] Filed: Jul. 9, 1992

Related U.S. Application Data

[63] Continuation of Ser. No. 699,361, May 13, 1991, abandoned.

[51] Int. Cl.$^5$ .............................................. C07C 2/22
[52] U.S. Cl. ................................ 585/532; 585/510; 585/520
[58] Field of Search ............... 585/510, 520, 511, 512, 585/532

[56] References Cited

U.S. PATENT DOCUMENTS

| | | | |
|---|---|---|---|
| 2,631,176 | 3/1953 | Heinrich | 260/683.15 |
| 3,637,503 | 1/1972 | Giannetti et al. | 252/59 |
| 3,725,498 | 4/1973 | Brennan | 260/683.15 B |
| 3,842,134 | 10/1974 | Pratt | 260/683.15 B |
| 3,907,924 | 9/1975 | Isa et al. | 260/683.15 D |
| 3,947,509 | 3/1976 | Isa et al. | 260/676 R |
| 3,952,071 | 4/1976 | Isa et al. | 260/683.15 B |
| 4,006,199 | 2/1977 | Isa et al. | 260/683.15 B |
| 4,031,158 | 6/1977 | Isa et al. | 260/683.15 B |
| 4,031,159 | 6/1977 | Mandai et al. | 585/532 |
| 4,066,715 | 1/1978 | Isa et al. | 585/532 |
| 4,107,080 | 8/1978 | Taniyasu et al. | 252/431 C |
| 4,973,788 | 11/1990 | Lin et al. | 585/512 |

OTHER PUBLICATIONS

Isa, H., "Catalysts for the Synthesis of Alpha Olefin Oligomer", JSL, (3), pp. 29–43.

*Primary Examiner*—Anthony McFarlane
*Attorney, Agent, or Firm*—David M. Bunnell

[57] ABSTRACT

Olefin oligomers are prepared by polymerizing one or a mixture of olefins, each of which has about 6 to 20 carbon atoms, in the presence of a catalyst prepared by reacting in an organic solvent an aluminum halide and from about 0.01 to 0.99 mole per mole of aluminum halide of a proton donor.

15 Claims, No Drawings

OLIGOMERIZATION OF ALPHA-OLEFIN

This application is a continuation of application Ser. No. 07/699,361, filed May 13, 1991 now abandoned.

BACKGROUND

This invention relates generally to the preparation of alpha-olefin oligomer oils having a high viscosity, and particularly to methods for preparing oligomer oils, which are useful in lubricants and functional fluids, by polymerizing an olefin having 6 or more carbon atoms in the presence of a catalyst prepared by reacting an aluminum halide such as $AlCl_3$ with a proton source, such as an alcohol, in an organic solvent.

Synthetic oils having high viscosities of about 30 centistokes or above at 100° C. have been prepared by using aluminum halide catalyst systems to oligomerize alpha-olefins having about 6 to 20 carbon atoms. Such oils possess a good stability to shearing, a low pour point, and a high viscosity index. A number of aluminum halide catalyst systems have been disclosed for this purpose. U.S. Pat. No. 3,637,503 discloses a lubricating oil composition containing a viscosity index improving amount of a polymer obtained by polymerizing a normal alphaolefin having from 4 to 16 carbon atoms in the presence of a mixture of aluminum chloride and a nonpolymerizing hydrocarbon diluent. The mixture is preferably contacted with gaseous hydrogen chloride as a promoter by bubbling the gas through the solvent containing the aluminum chloride prior to introducing the olefin monomer. We have found that the viscosity of the product polyolefin oil is very sensitive to the ratio of hydrogen chloride to aluminum chloride. It would be difficult to control this ratio to the extent necessary to provide oligomer products of a selected viscosity using gaseous hydrogen chloride according to the process of U.S. Pat. No. 3,637,503. U.S. Pat. No. 4,107,080 discloses the preparation of an oligomerization catalyst suitable for the preparation of low viscosity olefin polymers in which aluminum halide is contacted with a fatty acid with complete removal of the hydrogen halide which is generated. U.S. Pat. No. 4,006,199 describes a catalyst system using aluminum halides in conjunction with dicarbonyl compounds to give olefin oligomers having a kinematic viscosity between 500-1500 cSt at 37.6° C. U.S. Pat. No. 4,219,691 discloses the preparation of olefin oligomer in the presence of an aluminum halide and a secondary or tertiary alcohol. The optional use of a solvent in the oligomerization reaction for reducing the viscosity increase and easy control of the reaction temperature is suggested. Comparative i0 examples using primary alcohols gave relatively low viscosity products e.g. less than 500 centistokes at 37.8° C. U.S. Pat. No. 2,631,176 discloses the preparation of high viscosity olefin polymers using a Friedel-Crafts catalyst in the presence of an oxygenated compound such as an aliphatic alcohol. The preparation of a polymer of 1-deoene in the presence of n-heptane, $AlCl_3$ and about 2 moles of methanol per mole of $AlCl_3$ (excess methanol) is described. The polymer had a 210° F. viscosity of 232 SUS or only about 50 centistokes. We have discovered a process which can provide, with good selectivity, very high viscosity olefin oligomer fluids using a catalyst composition, which includes aluminum halide in combination with primary (as well as secondary and tertiary) alcohols or other proton donor compounds, by preparing the catalyst composition in the presence of an organic solvent using an excess of aluminum halide.

BRIEF SUMMARY

In accordance with this invention there is provided a process for preparing an olefin oligomer comprising polymerizing one or a mixture of olefins, each of which has about 6 to 20 carbon atoms, in the presence of a catalyst prepared by reacting, in an organic solvent, an aluminum halide with from about 0.01 to 0.99 mole per mole of aluminum halide of a proton source.

Also provided is a catalyst composition prepared by reacting, in an organic solvent, an aluminum halide with from about 0.01 to 0.99 mole per mole of aluminum halide of a proton source so as to generate hydrogen halide which is substantially completely absorbed in said solvent.

DETAILED DESCRIPTION

The olefins used in the process of the invention are predominately (at least 50 mole percent) $C_6$ to $C_{20}$ straight chain monoolefinically unsaturated hydrocarbons in which the olefinic unsaturation occurs in the 1- or alpha-position. Such olefins are commercially available and can be made by the thermal cracking of paraffinic hydrocarbons or by the well-known Ziegler ethylene chain growth and displacement process using triethyl aluminum. Individual olefins may be used as well as mixtures of such olefins. Examples of such olefins are 1-hexene, 1-octene, 1-nonene, 1-decene, 1-dodecene, 1-hexadecene and 1-tetradecene. The more preferred normal-alpha-olefin monomers are those containing about 8-12 carbon atoms. The most preferred olefin monomer is 1-decene.

The olefin monomers can also contain amounts of up to a total of about 50 but usually less that 25 mole percent of internal olefin and vinylidene olefin.

The catalysts for use in the present invention include an aluminum halide e.g. aluminum fluoride, aluminum bromide, aluminum chloride, aluminum iodide and mixtures thereof. The preferred aluminum halide is aluminum chloride. The aluminum halide is reacted with from about 0.01 to 0.99 mole per mole of aluminum halide of a proton source and, preferably, about 0.05 to 0.42 mole per mole of aluminum halide. It is necessary to carry out the reaction between the aluminum halide and the proton source in the presence of a nonpolymerizable organic solvent which acts to absorb the hydrogen halide which is generated. This permits the amount of hydrogen halide which is present in the oligomerization reaction to be reproducibly controlled to provide high viscosity oligomers products of from about 30 to 400 cSt at 100° C. by adjusting the proton source to aluminum halide ratio.

Both organic and inorganic proton sources which will generate hydrogen halide in contact with the aluminum halide can be used. These are, for example, proton donor compounds such as water, alcohols, phenols, e.g. phenol, naphthol, etc., carboxylic acids, inorganic acids, e.g. phosphoric, sulfuric, nitric, etc., and the like. Preferred proton sources are primary, secondary, and tertiary aliphatic and alicyclic alcohols and alcohol alkoxylates such as, for example, methanol, ethanol, propanol-1,isopropanol, butanol-1, tert.-butyl alcohol, sec.-butyl alcohol, pentane-2-ol, pentanol-1, hexanol-1, hexane-2-ol, cyclohexanol, heptanol-1, heptane-2-ol, octanol-1, decanol-1, ethylene glycol, propylene glycol, glycerol and the like; and any mixtures thereof. Preferred alcohol alkoxylates can be represented by the formula:

RO(CHR'—CHR''(CHR''')$_m$—O)$_n$H where m is 0, 1 or 2, R is hydrocarbyl containing 1 to 24 carbon atoms, including mixtures thereof, R', R'' and R''' are independently hydrogen, methyl, or ethyl, and when m is 2 each R''' can be different, and n averages 1 to 15. Examples of such alcohol alkoxylates include glycol ethers such as ethylene glycol monomethyl ether (2-methoxyethanol) and propylene glycol monoethyl ether and the like and ethoxylates derived from mixed $C_2$ to $C_{24}$, preferably $C_2$ to $C_{18}$ and most preferably $C_6$ to $C_{12}$ straight chain alcohols. Examples of carboxylic acids include propionic acid, butyric acid, trimethyl acetic acid, valeric acid, caproic acid, 2-ethyl hexanoic acid, caprilic acid, enanthic acid and the like.

Suitable solvents for use in preparing the catalysts are aprotic organic liquids and include, for example, aliphatic, alicyclic and halogenated hydrocarbons. Such solvents are inert in that they do not participate in the oligomerization reaction. Preferred solvents are n-pentane, n-heptane, isooctane, cyclohexane, decane, methylene chloride, dichloroethane and the like. The amount of organic solvent used should be sufficient to absorb substantially all of the hydrogen halide which is generated. Generally amounts of from about 20 to 500 percent by volume of the amount of olefin to be oligomerized in the process are adequate. The amount of aluminum halide catalyst can vary and amounts of from about 1 to 10 weight percent based on the amount of olefin are preferred. The amount of hydrogen halide in the reaction system is an important factor in determining the viscosity of the oligomer and in achieving high viscosity products. The viscosity is readily controlled according to the process of the invention by selecting the amount of proton source which is used to react with the aluminum halide in the solvent absorbent and thus generate the desired amount of hydrogen halide.

The reaction can be carried out by forming a slurry of the aluminum halide in the solvent absorbent, adding the proton donor co-catalyst and then feeding the olefin to a reactor which contains the catalyst system over a period of about 1 to 6 hours. The reaction temperatures will generally range from about 0° to 100° C. with the viscosity of the product decreasing somewhat with increasing temperature.

The invention is further illustrated by, but is not intended to be limited to, the following examples.

EXAMPLE 1

The reaction was carried out in a 500 ml five neck round bottom flask fitted with a mechanical stirrer, a solid addition funnel, a thermometer and $CaCl_2$ guard tube, a gas inlet tube and an addition funnel. The system was purged with dry nitrogen and 4.0 grams of aluminum chloride (4 weight percent of 1-decene) and 135 mL of heptane were added with stirring to form an aluminum chloride slurry. Methoxyethanol 0.57 grams (0.57 weight percent of 1-decene) was added to the slurry system using a syringe with a long needle submerged in the heptane. There was no gas evolution and 100 grams of 1-decene were then added over a period of 4 hours. The temperature was maintained between 25°–30° C. with an ice water bath. At the end of the reaction, the reaction mixture was poured into 200 mL of a 50:50 mixture of heptane and water with vigorous stirring. The heptane layer was then separated and washed with water (100/mL). Drying (MgSO$_4$), filtration and the removal of heptane gave a viscous oil. Flashing at 150° C./0.5 mm afforded the final product (96% conversion) which had a viscosity at 100° C. of 86.4 cSt. As a comparison, the procedure was repeated except that the methoxyethanol was added to dry aluminum chloride in the flask with evolution of HCl. The HCl was driven out by dry nitrogen before adding the 1-decene. The 1-decene was then added in heptane (1:1 volume). The product had a 100° C. viscosity of 63.3 cSt which was only slightly higher than the 54.1 cSt product viscosity achieved in the absence of solvent using the same catalyst and co-catalyst concentrations.

EXAMPLES 2–6

The procedure according to Example 1 was carried out at 25° C. with a 1:1 vol. ratio of 1-decene/n-heptane for 4 hours using 1-propanol at the catalyst compositions and concentrations shown in Table I The kinematic viscosities (in centistokes) and viscosity indexes (VI) are also reported in the Table.

TABLE I

| Example | AlCl$_3$ Conc. (Wt. %) | Alcohol Conc. (Wt %) | Viscosity, cSt 100° C. | 40° C. | VI |
|---|---|---|---|---|---|
| 2 | 1 | 0.18 | 53.6 | 561 | 158 |
| 3 | 2 | 0.18 | 64.6 | 715 | 161 |
| 4 | 3 | 0.18 | 79 | 885 | 169 |
| 5 | 4 | 0.18 | 84.4 | 961 | 170 |
| 6 | 6 | 0.18 | 88.4 | 1020 | 171 |

The results indicate that increasing the AlCl$_3$ concentration at a constant alcohol concentration produces a moderate increase in product viscosity.

EXAMPLES 7–14

The procedure according to Example I was carried out at 50° C. with a 1:1 volume ratio of 1-decene/n-heptane for four hours using aluminum chloride at 3 weight percent with varying amounts of 1-octanol. The results are reported in Table II.

TABLE II

| Example | AlCl$_3$ Conc. (Wt. %) | Alcohol Conc. (Wt. %) | Conversion (%) | KV100° C. (cSt) |
|---|---|---|---|---|
| 7 | 3 | 0.15 | 92 | 39.8 |
| 8 | 3 | 0.20 | 96 | 45.5 |
| 9 | 3 | 0.46 | 95 | 75.3 |
| 10 | 3 | 0.56 | 95 | 87.0 |
| 11 | 3 | 0.70 | 94 | 101.0 |
| 12 | 3 | 0.72 | 94 | 86.9 |
| 13 | 3 | 0.74 | 93 | 77.5 |
| 14 | 3 | 0.83 | 95 | 75.0 |

The results indicate that at a constant AlCl$_3$ concentration the product viscosity (cSt) was increased by increasing the alcohol concentration and then leveled off and declined after a certain point.

The procedure according to Example 1 was carried out at 25° C with a 1:1 volume ratio of 1-decene/n-heptane for 4 hours using aluminum chloride at 4 weight percent and 1.25 mol percent of the different alcohols The results are reported in Table III.

TABLE III

| Example | ROH | 100° C. Vis. (cSt) | 40° C. Vis. (cSt) | VI |
|---|---|---|---|---|
| 15 | MeOH | 359 | 4610 | 235 |
| 16 | PrOH | 302 | 3890 | 224 |
| 17 | BuOH | 214 | 2780 | 204 |

TABLE III-continued

| Example | ROH | 100° C. Vis. (cSt) | 40° C. Vis. (cSt) | VI |
|---|---|---|---|---|
| 18 | n-Decanol | 165 | 2140 | 191 |

The results indicate that the product viscosity decreased with increased molecular weight of the alcohol.

EXAMPLES 19-21

The procedure according to Example 1 was carried out at 25° C. with varying ratios of n-heptane solvent at 3 weight percent AlCl$_3$/0.20 weight percent of 1-propanol for 4 hours. The results are reported in Table IV.

TABLE IV

| Example | Sol:decene Vol. | 100° C. Vis. cSt | 40° C. Vis. cSt | VI |
|---|---|---|---|---|
| 19 | 1:1 | 79 | 885 | 169 |
| 20 | 1:2 | 68 | 732 | 167 |
| 21 | 1:4 | 72 | 786 | 167 |

EXAMPLE 22

Example 19 was repeated at 50° C. and the product had a 100° C. viscosity of 63 cSt.

What is claimed is:

1. A process for preparing an olefin oligomer comprising polymerizing one or a mixture of olefins, each of which has about 6 to 20 carbon atoms, in the presence of a catalyst prepared by reacting, in an organic solvent, an aluminum halide with an alcohol in proportions of from about 0.05 to 0.42 mol of alcohol per mole of aluminum halide such that said solvent absorbs hydrogen halide which is generated in said reaction so as to provide a controlled amount of hydrogen halide in the polymerization to produce an olefin oligomer having a kinematic viscosity of from about 30 to 400 cSt at 100° C.

2. A process according to claim 1 wherein the amount of alcohol ranges from about 0.05 to 0.28 mol per mole of aluminum halide.

3. A process according to claim 2 wherein the amount of aluminum halide ranges from about 1 to 10 weight percent of the olefin.

4. A process according to claim 1 wherein said olefins are selected from octene-1, decene-1, dodecene-1 and tetra-decene-1.

5. A process according to claim 1 wherein said alcohol is a primary alcohol having 1 to 20 carbon atoms.

6. A process according to claim 1 wherein said alcohol is an alcohol alkoxylate.

7. A process according to claim 6 wherein said alcohol alkoxylate has the formula:

$$RO(CHR'-CHR''(CHR'')_m-O)_nH$$

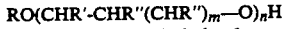

where m is 0, 1 or 2, R is hydrocarbyl containing 1 to 24 carbons, including mixtures thereof, R', R'' and R''' are independently hydrogen, methyl, or ethyl and when m is 2 each R''' can be different, and n averages 1 to 15.

8. A process according to claim 5 wherein said alcohol is 1-octanol.

9. A process according to claim 1 wherein said aluminum halide is AlCl$_3$.

10. A process according to claim 2 wherein said aluminum halide is AlCl$_3$.

11. A process according to claim 6 wherein said aluminum halide is AlCl$_3$.

12. A process according to claim 1 wherein said solvent is selected from aliphatic, alicyclic and/or halogenated hydrocarbons.

13. A process for preparing an olefin oligomer having a selected kinematic viscosity of from about 30 to 400 cSt at 100° C. comprising polymerizing an olefin selected from the group consisting of octene-1, decene-1, dodecene-1, tetradencene-1 and mixtures thereof in the presence of a catalyst prepared by reacting, in an organic solvent, aluminum chloride and an alcohol in proportions of from about 0.05 to 0.42 mole of alcohol per mole of aluminum chloride such that said solvent absorbs Hcl generated in said reaction so as to provide a controlled amount of HCl in the polymerization.

14. The process of claim 13 wherein said alcohol is 1-octanol and said selected kinematic viscosity is about 100 cSt at 100° C.

15. The process of claim 13 wherein said alcohol is 1-octanol and said selected kinematic viscosity is about 40 cSt at 100° C.

* * * * *